(12) United States Patent
Gupta

(10) Patent No.: US 9,333,280 B2
(45) Date of Patent: *May 10, 2016

(54) STABILIZED ENZYME COMPOSITIONS

(71) Applicant: Teleflex Medical Incorporated, Durham, NC (US)

(72) Inventor: Nisha Gupta, Audubon, PA (US)

(73) Assignee: Teleflex Medical Incorporated, Durham, NC (US)

(*) Notice: Subject to any disclaimer, the term of this patent is extended or adjusted under 35 U.S.C. 154(b) by 232 days.

This patent is subject to a terminal disclaimer.

(21) Appl. No.: 14/041,947

(22) Filed: Sep. 30, 2013

(65) Prior Publication Data

US 2014/0030303 A1    Jan. 30, 2014

Related U.S. Application Data

(63) Continuation-in-part of application No. 12/392,544, filed on Feb. 25, 2009, now Pat. No. 8,545,459.

(51) Int. Cl.
| | |
|---|---|
| *A61L 33/06* | (2006.01) |
| *A61L 33/04* | (2006.01) |
| *A61L 29/04* | (2006.01) |
| *A61L 29/08* | (2006.01) |
| *A61L 29/16* | (2006.01) |
| *A61L 33/00* | (2006.01) |

(52) U.S. Cl.
CPC ............. *A61L 33/062* (2013.01); *A61L 29/048* (2013.01); *A61L 29/085* (2013.01); *A61L 29/16* (2013.01); *A61L 33/0047* (2013.01); *A61L 2300/206* (2013.01); *A61L 2300/254* (2013.01); *A61L 2300/404* (2013.01); *A61L 2300/42* (2013.01); *A61L 2300/45* (2013.01)

(58) Field of Classification Search
None
See application file for complete search history.

(56) References Cited

U.S. PATENT DOCUMENTS

| | | | |
|---|---|---|---|
| 4,273,873 | A | 6/1981 | Sugitachi et al. |
| 4,305,926 | A | 12/1981 | Everse et al. |
| 4,378,435 | A | 3/1983 | Takagi et al. |
| 4,483,922 | A | 11/1984 | Carpenter et al. |
| 4,764,466 | A | 8/1988 | Suyama et al. |
| 5,380,299 | A | 1/1995 | Fearnot et al. |

(Continued)

FOREIGN PATENT DOCUMENTS

| | | |
|---|---|---|
| CA | 2579458 A1 | 8/2007 |
| EP | 0391400 A2 | 10/1990 |
| EP | 0200966 B1 | 7/1993 |
| EP | 0952215 A2 | 10/1999 |
| EP | 1911470 A1 | 4/2008 |
| JP | 55034082 A | 3/1980 |
| JP | 61238732 A | 10/1986 |
| WO | 2008150375 A1 | 12/2008 |

OTHER PUBLICATIONS

Fujishima et al., "Controlled Trial of Combined Urokinase and Dextran Sulfate Therapy in Patients with Acute Cerebral Infarctio", Angiology, Westminster Publications, Inc., Glen Head, NY, US, vol. 37, No. 7, Jul. 1, 1986, pp. 487-498.

(Continued)

*Primary Examiner* — Manjunath Rao
*Assistant Examiner* — William W Moore
(74) *Attorney, Agent, or Firm* — Baker Hostetler LLP

(57) ABSTRACT

A medical device includes a base material having an immobilized enzyme and dextran sulfate. The dextran sulfate has a molecular weight that is less than 40 kilo dalton (kDa). The medical device is formed from at least a base material. An enzyme is immobilized on the base material. The enzyme is stabilized with a dextran sulfate having a molecular weight of less than 40 (kDa).

18 Claims, 3 Drawing Sheets

(56) References Cited

U.S. PATENT DOCUMENTS

| | | | |
|---|---|---|---|
| 5,451,424 | A | 9/1995 | Solomon et al. |
| 5,688,516 | A | 11/1997 | Raad et al. |
| 5,707,366 | A | 1/1998 | Solomon et al. |
| 6,248,712 | B1 | 6/2001 | Danoe et al. |
| 6,255,277 | B1 * | 7/2001 | Stamler et al. ............ 424/484 |
| 6,261,271 | B1 | 7/2001 | Solomon et al. |
| 6,273,875 | B1 | 8/2001 | Siman et al. |
| 6,416,546 | B1 | 7/2002 | Kimura et al. |
| 6,417,173 | B1 | 7/2002 | Roufa et al. |
| 6,528,107 | B2 | 3/2003 | Chinn et al. |
| 6,663,606 | B1 | 12/2003 | Barry et al. |
| 8,545,459 | B2 * | 10/2013 | Gupta et al. ............ 604/266 |
| 2004/0106912 | A1 | 6/2004 | Rosinskaya et al. |
| 2004/0137065 | A1 | 7/2004 | Vogt et al. |
| 2004/0208908 | A1 * | 10/2004 | Modak et al. ............ 424/423 |
| 2004/0224001 | A1 | 11/2004 | Pacetti et al. |
| 2005/0191333 | A1 | 9/2005 | Hsu |
| 2005/0197364 | A1 | 9/2005 | Kelly et al. |
| 2006/0257390 | A1 | 11/2006 | Semba |
| 2007/0083230 | A1 | 4/2007 | Javois |
| 2007/0104758 | A1 | 5/2007 | Hamilton et al. |
| 2007/0129690 | A1 * | 6/2007 | Rosenblatt et al. ....... 604/265 |
| 2007/0212344 | A1 | 9/2007 | Preissner et al. |
| 2008/0188830 | A1 | 8/2008 | Rosenblatt et al. |
| 2009/0130171 | A1 | 5/2009 | Do et al. |
| 2009/0155335 | A1 * | 6/2009 | O'Shaughnessey et al. . 424/423 |
| 2009/0171435 | A1 * | 7/2009 | Kuppurathanam et al. .. 623/1.12 |
| 2009/0264880 | A1 * | 10/2009 | Solem ..................... 606/41 |
| 2009/0326580 | A1 * | 12/2009 | Anderson et al. .......... 606/246 |
| 2010/0069854 | A1 | 3/2010 | Okoh et al. |
| 2010/0082097 | A1 | 4/2010 | Rosenblatt et al. |
| 2010/0189808 | A1 | 7/2010 | Gupta et al. |
| 2010/0196434 | A1 | 8/2010 | Gupta et al. |
| 2010/0215711 | A1 | 8/2010 | Gupta et al. |
| 2010/0233288 | A1 | 9/2010 | Gupta et al. |
| 2010/0268174 | A1 | 10/2010 | Steinke et al. |

OTHER PUBLICATIONS

Chin, et al., "Antimicrobial Activities of Ceragenins against Clinical Isolates of Resistant *Staphylococcus aureus*", Antimicrobial Agents Chemotherapy, vol. 51, No. 4, pp. 1268-1273, (Apr. 2007).

International Search Report and the Written Opinion of the International Searching Authority, or the Declaration of International Application No. PCT/US14/57984, mailed Mar. 19, 2015.

Jianjiang Hu, et al., "Functionalization of Poly(ethylene terephthalate) Film by Pulsed Plasma Deposition of Maleic Anhydride", Advanced Functional Materials, Sep. 2003, pp. 692-697, vol. 13—issue No. 9, WILEY-VCH Verlag GmbH & Co. KGaA, Weinheim.

Christoph Harter, et al., "Catheter-Related Infection and Thrombosis of the Internal Jugular Vein in Hematologic-Oncologic Patients Undergoing Chemotherapy: A Prospective Comparison of Silver-Coated and Uncoated Catheters", Cancer, Jan. 1, 2002, pp. 245-251, vol. 94—issue No. 1.

David J. Kuter, "Thrombotic Complications of Central Venous Catheters in Cancer Patients", The Oncologist, 2004, pp. 207-216, vol. 9.

Matsuo, O., et al., 1980, "Effect of low molecular weight dextran sulfate on plasmin activity measured with S-2251", Acta Physiologica Latinoamericana, vol. 30, No. 3, pp. 193-198.

Raad, I. I, et al., 1994, "The relationship between the thrombotic and infectious complications of central venous catheters", Journal of the American Medical Association, vol. 271, pp. 1014-1016.

Mermel, L. A., 2000, "Prevention of intravascular catheter-related infections", Annals of Internal Medicine, vol. 132, No. 5, pp. 391-402.

Saint, S., et. al., 2000, "The clinical and economic consequences of nosocomial central venous catheter-related infection: are antimicrobial catheters useful?", Infection Control and Hospital Epidemiology, vol. 21, No. 6, pp. 375-380.

Safdar, N., et al. 2004, "The pathogenesis of catheter-related bloodstream infection with noncuffed short-term central venous catheters", intensive Care Medicine, vol. 30, No. 1, pp. 62-67.

Carrasco, M. N., et al., 2004, "Evaluation of a triple-lumen central venous heparin-coated catheter versus a catheter coated with chlorhexidine and sliver sulfadiazine in critically ill patients", Intensive Care Medicine, vol. 30, pp. 633-638.

Van Rooden, C. J., et al., 2005, "Infectious complications of central venous catheters increase the risk of catheter-related thrombosis in hematology patients: A prospective study", Journal of Clinical Oncology, vol. 23, No. 12, pp. 2655-2660.

Hanna, H., et al., 2006, "Comparative in vitro efficacies and antimicrobial durabilities of novel antimicrobial central venous catheters", Antimicrobial Agents and Chemotherapy, vol. 50, No. 10, pp. 3283-3288.

Long, D. A., et al., 2006, "Effect of heparin-bonded central venous catheters on the incidence of catheter-related thrombosis and infection in children and adults", Anaesthesia and Intensive Care, vol. 34, No. 4, pp. 481-484.

* cited by examiner

STABILIZED ENZYME COMPOSITIONS

CROSS-REFERENCE TO RELATED APPLICATIONS

This application claims priority to and is a continuation-in-part application of U.S. patent application entitled "STABILIZED ENZYME COMPOSITIONS," filed Feb. 25, 2009, having Ser. No. 12/392,544, now pending, the disclosure of which is hereby incorporated by reference in its entirety.

FIELD OF THE INVENTION

The present invention generally relates to enzyme compositions. More particularly, the present invention pertains to stabilized enzyme compositions, medical devices having stabilized enzyme compositions, and method of production thereof.

BACKGROUND OF THE INVENTION

Implantable medical devices such as tunneled catheters play a major role in general medicine. Within days of insertion, almost all central venous catheters are coated with a fibrin sheath, and within 30 clays, most catheter-related thrombi arise. (See C Harter, H J Salwender, A Bach, G Egerer, H Goldschmidt and A D Ho (2002) Catheter-related infection and thrombosis of the internal jugular vein in hematologic-oncologic patients undergoing chemotherapy: a prospective comparison of silver-coated and uncoated catheters. *Cancer* 94: 245-251.) Aside from reducing the function of the catheter, these catheter-related thrombi can cause postphlebitic syndrome in 15%-30% cases and pulmonary embolism in 11% of the cases. (See D J Kuter (2004) Thrombotic Complications of Central Venous Catheters in Cancer Patients. *The Oncologist* 9: 207-216.)

To minimize the risk of thrombosis, immobilization of fibrinolytic enzymes such as Urokinase (uPA) on the surface of implantable medical devices such as tunneled catheters has been described. Examples of immobilized fibrinolytic enzymes are disclosed in U.S. Pat. Nos. 4,305,926, 4,273,873, 4,378,435, and 5,380,299. Unfortunately, the fibrinolytic activity from such devices, e.g. urokinase coated hemodialysis catheter from Unitika (Blood access UK-catheter, Unitika), is retained for less than two weeks. This duration is insufficient for long term or chronic devices. A variety of agents have been conventionally utilized to stabilize fibrinolytic enzymes in solution. Examples of agents utilized to stabilize fibrinolytic enzymes in solution are disclosed in the following foreign patents: Japanese Patent No. JP61238732A2; European Patent No. EP0200966B1; Canadian Patent No. CA2579458AA; European Patent No. EP0391400 A2; and Japanese Patent No. JP55034082A2. However, to date, these agents have not been successfully utilized in an implantable medical device.

Accordingly, it is desirable to provide an implantable medical device having extended thrombolytic properties that is capable of overcoming the disadvantages described herein at least to some extent.

SUMMARY OF THE INVENTION

The foregoing needs are met, to a great extent, by the present invention, wherein in one respect a composition and method of stabilizing fibrinolytic enzymes on a medical device is provided and in another respect an implantable medical device having extended thrombolytic properties is provided.

An embodiment of the present invention pertains to a medical device. The medical device includes a base material having an immobilized enzyme covalently bound to the base material and dextran sulfate. The medical device is for vascular implantation in a patient. The dextran sulfate having a molecular weight that is about 8 kilodaltons (kDa) to stabilize the enzyme when in contact with blood of the patient.

Another embodiment of the present invention relates to a medical device. The medical device includes a polyurethane base material, an amount of a blood clot digestive enzyme, an amount of an extracellular matrix digestive enzyme, a low molecular weight dextran sulfate, and an antimicrobial agent. The polyurethane base material is for vascular implantation in a patient. The amount of the blood clot digestive enzyme is sufficient to reduce the formation of device related blood clots. The amount of the extracellular matrix digestive enzyme is sufficient to reduce neo-initimal hyperplasia. The enzymes are immobilized by covalently binding the enzymes to the base material. The low molecular weight dextran sulfate is to stabilize the enzymes when in contact with blood of the patient. The low molecular weight dextran sulfate has a molecular weight of about 8 kilodaltons. The antimicrobial agent is disposed in the polyurethane base material in an amount sufficient to reduce microbial growth.

Yet another embodiment of the present invention pertains to a medical device. The medical device includes a polyurethane base material, an amount of an enzyme, a low molecular weight dextran sulfate, and a chlorhexidine base or a pharmaceutically acceptable salt thereof. The polyurethane base material is for vascular implantation in a patient. The amount of the enzyme is sufficient to reduce the formation of blood clots in a patient or sufficient to reduce neo-initimal hyperplasia. The enzyme is covalently immobilized in the base material. The low molecular weight dextran sulfate is to stabilize the enzyme when in contact with blood of the patient. The low molecular weight dextran sulfate has a molecular weight of about 8 kilodaltons. The chlorhexidine base or a pharmaceutically acceptable salt thereof is disposed in the polyurethane base material in an amount sufficient to reduce microbial growth.

Yet another embodiment of the present invention related to a method of fabricating a medical device. In this method, the medical device is formed for vascular implantation in a patient from at least a base material. An enzyme is immobilized by covalently binding the enzyme on the base material. The enzyme is at least one of a blood clot digestive enzyme and an extracellular matrix digestive enzyme. The enzyme is stabilized when in contact with blood of the patient with a dextran sulfate having a molecular weight of about 8 kilodaltons.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
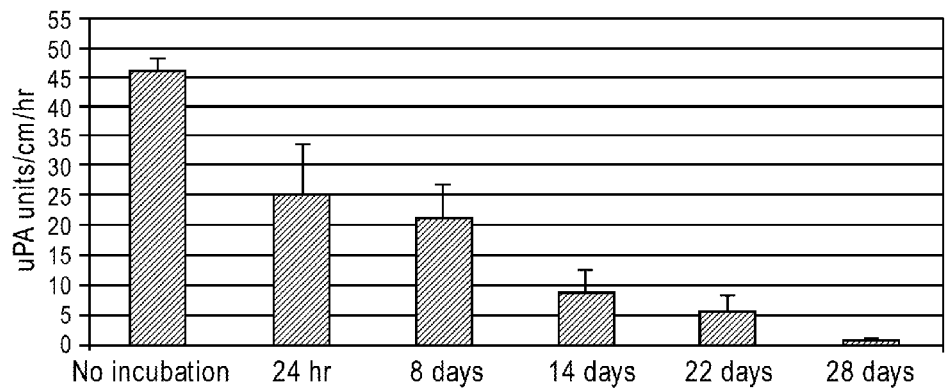
FIG. 1 is a graph showing fibrinolytic activity of a urokinase-type plasminogen activator (uPA) immobilized on polyurethane catheter segments following incubation times ranging from 0 to 28 days.

Embodiments of the invention provide an implantable medical device having extended enzymatic and/or antimicrobial properties. In various embodiments, these extended enzymatic and/or antimicrobial properties may be achieved via the immobilization of various suitable enzymes and/or antimicrobial agents on the surface of the implantable medical devices in the presence of dextran sulfate. Examples of suitable enzymes include blood clot digestive enzyme or fibrinolytic enzymes such as Urokinase (uPA), aminopeptidases, tissue plasminogen activator (tPA), streptokinase, and the like. Other suitable enzymes include extracellular matrix digestive enzyme such as: a protease; an aminopeptidase; a collagenase; a matrix metalloproteinase; a metalloendopeptidase; a serine endopeptidase; a hydrolase; a glucuronidase; a hyaluronoglucosaminidase; a heparanase; a cathepsin; a hyaluronidase; a matriptas; and the like. Examples of suitable antimicrobial agents include; Chlorhexidine base, Alexidine, other guanides including polyhexamethylene biguanide (PHMB), cationic selective antimicrobials (CSAs), Ceragenins, and the like. Two molecular weight ranges of dextran sulfate are worth distinguishing. The first molecular weight range is generally referred to as high molecular weight dextran sulfate ("HMW-DexS") which has a molecular weight of greater than 40,000 dalton (Da) to about 500,000 Da or more. HMW-DexS has previously reported to inhibit inflammatory cell invasion around an implant. The second molecular weight range is generally referred to as low molecular weight dextran sulfate ("LMW-DexS") which has a molecular weight of less that about 40,000 Da to about 500 Da. The beneficial use of LMW-DexS on an implant has not been previously reported. It is therefore surprising and unexpected that LMW-DexS stabilizes and increases the duration of bioactivity of immobilized fibrinolytic enzymes and/or releasable antimicrobial agent(s) on the surface of a medical device that interfaces with blood. As described herein, particular example is made of LMW-DexS having a molecular weight of about 8,000 Da. However, it is to be understood that LMW-DexS having a molecular weight of about 1,000, 2,000, 4,000, 10,000, and 20,000 Da are also within the purview of embodiments of the invention. Advantages of various embodiments of the present invention include: 1) improvements in the biodurability of covalently immobilized fibrinolytic enzymes; 2) optimization of LMW-DexS/fibrinolytic enzyme compositions; 3) stabilization of immobilized fibrinolytic enzyme structure; 4) compatibility of the stabilized and immobilized fibrinolytic enzymes with antimicrobial agents such as chlorhexidine (CHX), gentian violet (GV), and/or brilliant green.

In addition, it is within the purview of this and other embodiments of the invention that other suitable agents may be incorporated into the bulk material. Examples of suitable agents includes other antimicrobial agents, antibiotics, antiseptics, chemotherapeutics, antimicrobial peptides, mimetics, antithrombogenic, fibrinolytic, anticoagulants, anti-inflammatory, anti-pain, antinausea, vasodilators, antiproliferatives, antifibrotics, growth factors, cytokines, antibodies, peptide and peptide mimetics, nucleic acids, and/or the like.

Medical devices suitable for use with various embodiments of the invention may include catheters, tubes, sutures, nonwoven, meshes, drains, shunts, stents, foams etc. Other devices suitable for use with embodiments of the invention include those that may interface with blood, blood products, and/or fibrinogenic fluids, tissues, and/or products. In various embodiments, the fibrinolytic enzyme and/or dextran sulfate may be incorporated in or on all or part of the medical device. In a particular example, the fibrinolytic enzyme and 8 kDa LMW-DexS may be applied to the tip area of a vascular catheter. In this manner, the amount of the relatively expensive enzyme may be reduced without adversely affecting the efficacy of the vascular catheter. Benefits of one or more embodiments of this invention include the stabilization and increase in the duration of bioactivity of immobilized fibrinolytic enzymes and/or releasable agent(s) on the surface of a medical device that interfaces with blood.

Forms of chlorhexidine suitable for use with embodiments of the invention include chlorhexidine base, pharmaceutically acceptable chlorhexidine salts such as, for example, diacetate, laurate (dodecanoate), palmitate (hexadecanoate), myristate (tetradecanoate), stearate (octadecanoate) and/or the like. In addition, while particular examples are made of chlorhexidine base, chlorhexidine diacetate, and chlorhexidine dodecanoate, embodiments of the invention are not limited to any one form. Instead, as used herein, the term, 'chlorhexidine' refers to any one or a mixture of chlorhexidine base, pharmaceutically acceptable chlorhexidine salts such as, for example, diacetate, dodecanoatc, palmitate, myristate, stearate and/or the like. For example, other suitable chlorhexidine salts are to be found in U.S. Pat. No. 6,706,024, entitled Triclosan-Containing Medical Devices, issued on Mar. 16, 2004, the disclosure of which is hereby incorporated in its entirety. In general, suitable concentrations of chlorhexidine include a range from about 0.1% weight to weight (wt/wt) to about 30% wt/wt. More particularly, a suitable chlorhexidine range includes from about 3% wt/wt to about 20% wt/wt.

Suitable base materials generally include elastomers and/or polymer materials. Specific examples of suitable base materials include polyurethanes, polyvinylchlorides, thermoplastics such as, for example, fluoropolymers, vinyl polymers, polyolephins, copolymers, and/or the like.

In the following experiments, a duration of fibrinolytic activity is determined for urokinase-type plasminogen activator (uPA) immobilized on polyurethane catheter segments is determined. In addition, the unexpected improvements in the duration of fibrinolytic activity are determined for dextran sulfate stabilized uPA immobilized on polyurethane catheter segments is determined. We further show the unexpected improvements in the duration of fibrinolytic activity and antimicrobial activity when low molecular weight dextran sulfate is combined with uPA and an antimicrobial agent such as chlorhexidine and/or gentian violet.

Methods

Experiment 1

Immobilizing an Enzyme on Polyurethane Catheters, and Determining the Duration of Enzymatic Activity To immobilize an enzyme, polyurethane catheter segments were treated with 1% Butadiene Maleic Anhydride (BMA 1:1 ratio) polymer (25% solution in acetone, Polysciences, Warrington Pa.) and 1% Polyethylene glycol 400 (PEG 400, Hampton Research, Aliso Viejo Calif.) in acetone followed by curing at 90-100° C. for 3 hours under vacuum. Subsequently, the cured segments were incubated for 18 hours in sodium acetate buffer containing an enzyme, such as urokinase-type plasminogen activator (uPA), Streptokinase (SK), tissue plasminogen activator (tPA), collagenase, protease, aminopeptidase, matrix metalloproteinase, metalloendopeptidase, serine endopeptidase, a hydrolase, glucuronidase, hyaluronoglucosaminidase, heparanase, cathepsin, hyaluronidase, and matriptase, at 10-100 units/µl depending on the type of enzyme used. Thereafter, the segments were rinsed with phosphate buffered saline twice and finally with deionized water.

To test the durability of the activity from the immobilized enzyme, the catheters segments were incubated at 37° C. in citrated human plasma for different time periods. The citrated human plasma was replaced with fresh plasma after every 7 days. The activity of the enzyme immobilized on a catheter surface was lost within 28 days, as shown for immobilized uPA in FIG. 1.

Experiment 2

Figure 2:
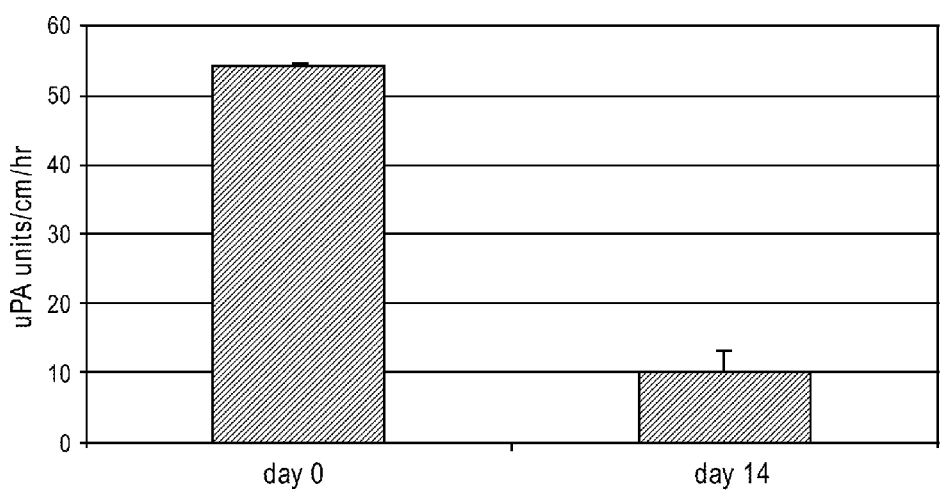
FIG. 2 is a graph showing urokinase activity of explanted catheter segments following incubation times of 0 and 14 days.

Determining In Vivo Performance of a Catheter with Immobilized Enzyme Implanted in the Superior Vena Cava of a Rabbit To assess in viva performance of the catheters with immobilized uPA, single lumen size 6 French (Fr) catheters were implanted in the superior vena cava of rabbits for 14 days. Urokinase (uPA) activity was measured on the surface of explanted catheters via a chromogenic assay as is well known to those skilled in the art. As shown in FIG. 2, the catheters retained about 20% of the original activity at day 14. The in vivo results correspond well with the amount of activity lost in vitro after fourteen days of incubation in human plasma (FIG. 1).

Experiment 3

Evaluating Compounds for Improving the Performance of the Catheters with Enzymatic Activity Various compounds were evaluated for improving the duration of enzymatic activity from a catheter with immobilized enzyme. These compounds included: 1) low molecular weight dextran sulfate (LMW-DexS) with molecular weight of 8 kilo dalton (8 kDa); 2) human serum albumin (HSA); and 3) arginine. In this test, either 1 milligram/milliliter (mg/mL) of HSA or 1% weight/volume (w/v) of LMW-DexS (8 kDa) was added to a solution of sodium acetate buffer containing an enzyme at 10-100 units/µl. Either of the above solution was used to incubate BMA/PEG treated catheter segments. In addition, segments treated with BMA/PEG and the enzyme were rinsed in saline and, subsequently dipped in an aqueous solution containing 0.01% arginine as described in U.S. Pat. No. 4,764,466, entitled Method for stabilizing an immobilized fibrinolytic enzyme, issued on Aug. 16, 1988, the disclosure of which is hereby incorporated in its entirety.

Figure 3:
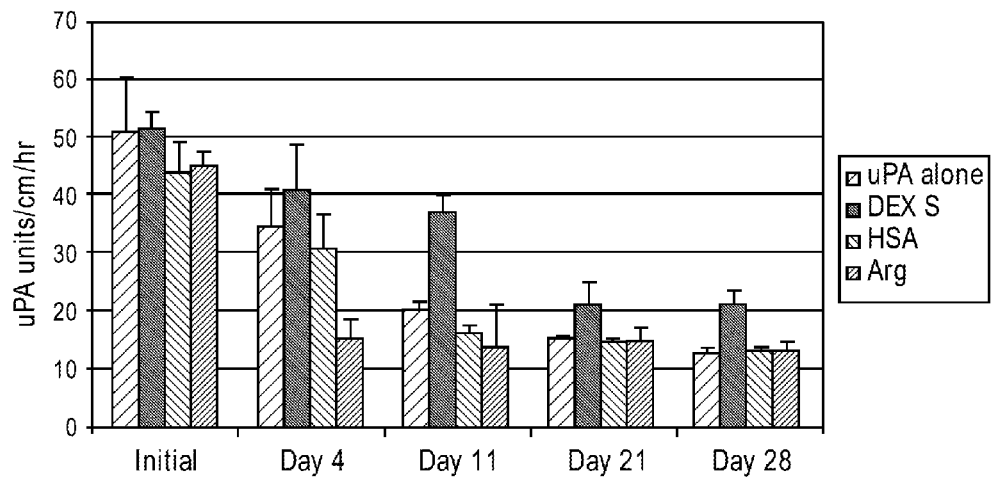
FIG. 3 is a graph showing fibrinolytic activity of uPA immobilized on polyurethane catheter segments and stabilized with low molecular weight dextran sulfate, human serum albumin, and the amino acid arginine following incubation times ranging from 0 to 28 days.

As shown in FIG. 3, LMW-DexS (8 kDa) treated segments with immobilized uPA retained the highest enzyme activity after 28 days of incubation in water at 37° C. compared to the other treatments.

Experiment 4

Evaluating Compounds for Improved Performance of the Enzymatic Catheters Containing an Antimicrobial Agent As disclosed in U.S. Pat. Nos. 5,688,516, 6,273,875, and 6,528,107, medical devices may be treated with antimicrobial agents together with an enzyme to provide dual benefits. However, to date, no known research has been conducted to examine the use of LMW-DexS (8 kDa) to improve the biodurability of implantable medical devices with antimicrobial agents together with an enzyme. To test if LMW-DexS (8 kDa) has similar stabilizing effect on an immobilized enzyme, such as uPA in presence of an antimicrobial agent, polyurethane catheters were dip coated in a polymer solution containing either chlorhexidine diacetate (CHA) or chlorhexidine dodecanoate (CHDD) and dried overnight at room temperature. The CHA or CHDD coated catheters were subsequently dipped in BMA/PEG solution for 30 seconds and then cured for 3 hours at 90-100° C. under vacuum. Thereafter the cured segments were incubated in urokinase solution containing HSA, LMW-DexS (8 kDa) or arginine as in the earlier experiment.

Figure 4:
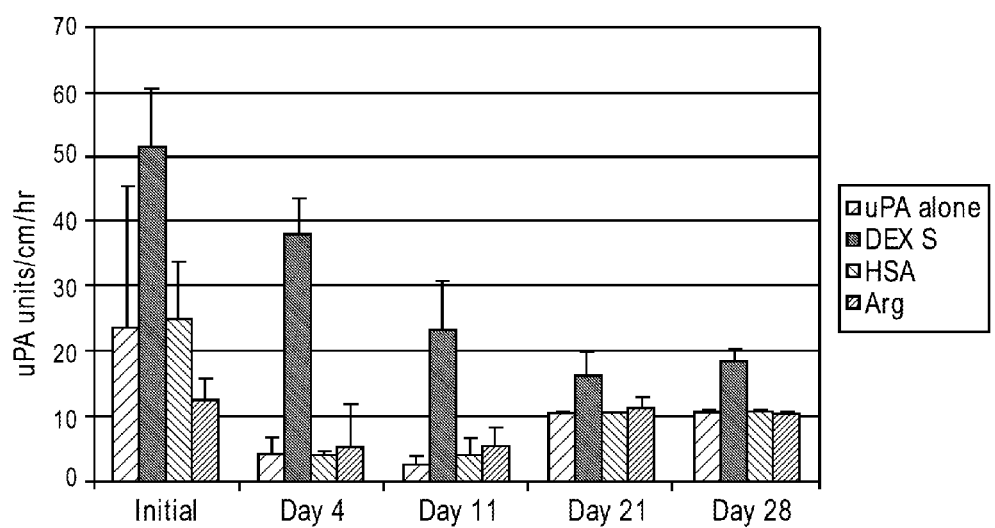
FIG. 4 is a graph showing fibrinolytic activity of uPA immobilized on chlorhexidine coated polyurethane catheter segments and stabilized with low molecular weight dextran sulfate, human serum albumin, and the amino acid arginine following incubation times ranging from 0 to 28 days.

As shown in FIG. 4, of the three agents tested, LMW-DexS (8 kDa) treated segments maintained the highest uPA activity after 28 days of incubation in water.

Experiment 5

Evaluating the Use of Maleic Anhydride to Attach an Enzyme to the Catheters Containing an Antimicrobial Agent Thin films rich in anhydride groups can be created by pulsed plasma polymerization of maleic anhydride. (See J Hu et al (2003) Functionalization of poly(ethylene terephthalate) film by pulsed plasma deposition of maleic anhydride. Advanced Functional Materials 13: 692-697.) The plasma of maleic anhydride was utilized as a method to introduce anhydride groups for enzyme attachment on to the CHA/polyurethane surface. This method of enzyme attachment is generally known to those skilled in the art and thus, in the interest of brevity, is only briefly described herein. Polyurethane catheters were dip coated in a polymer solution containing CHA, dried overnight at room temperature, treated with maleic anhydride (Sigma-Aldrich Corp. St. Louis Mo.) plasma generated under Argon atmosphere in a plasma chamber (Diener Electronics, Reading Pa.). The plasma deposition reactions were carried out at a pressure of 15 Pascal (Pa), 90 Watts (W) peak power for 5 minutes or for ten cycles of 12 seconds each. Subsequently, catheter segments were incubated for 18 hours in sodium acetate buffer, pH 5 containing 30 units/µl uPA with or without 1% LMW-DexS (8 kDa). Catheter segments were rinsed in phosphate buffered saline (PBS) twice and then in deionized water before incubation in citrated human plasma for durability testing. After 28 days of incubation in human plasma, enzymatic (fibrinolytic) activity of catheter segments was assessed by a clot lysis method. The clots were made as follows: 9% fibrinogen and 1.7 units/mL of plasminogen were incubated at 37° C. for 5 minutes in 197 millimolar (mM) borate/borax buffer, pH 7.5 containing 0.9% (w/v) sodium chloride and 0.5% (w/v) gelatin. Subsequently, 100 units/mL of thrombin was added to initiate the fibrin polymerization and clot formation.

Figure 5:
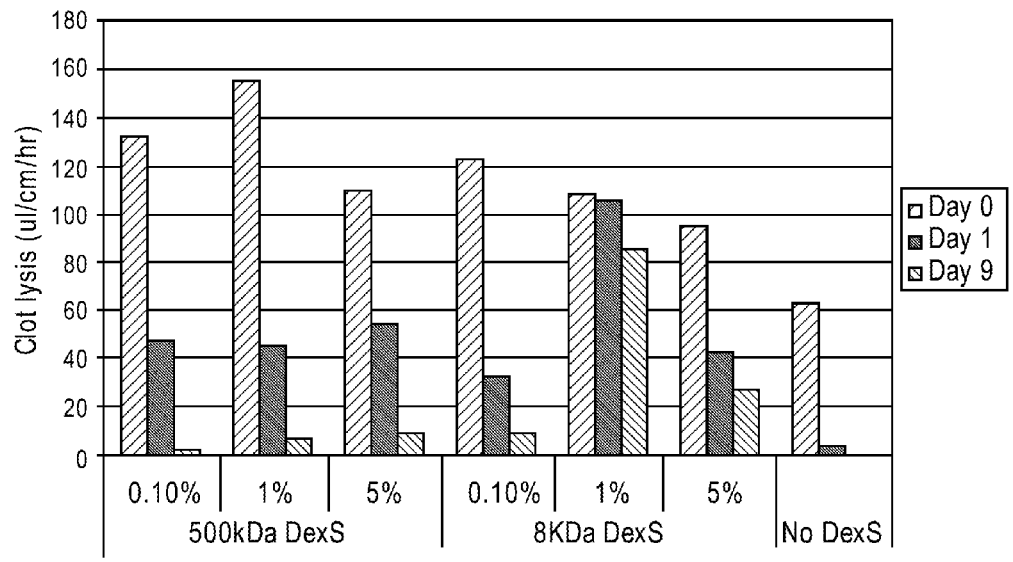
FIG. 5 is a graph showing fibrinolytic activity of uPA immobilized on chlorhexidine coated TECOTHANE® catheter segments and stabilized with high molecular weight dextran sulfate and low molecular weight dextran sulfate following incubation times ranging from 0 to 9 days.

To conduct the clot lysis assay, a 0.5 cm long catheter segment was placed on a clot for 6 hours at 37° C. and the volume of lysed clot was recorded. This procedure was performed for each sample shown in FIG. 5. As shown in FIG. 5, approximately an eight fold higher clot lysis was achieved when 1% LMW-DexS (8 kDa) was included as enzyme stabilizer compared to high molecular weight dextran sulfate or absence of dextran sulfate after 9 days of soaking in human plasma.

Experiment 6

Figure 6:
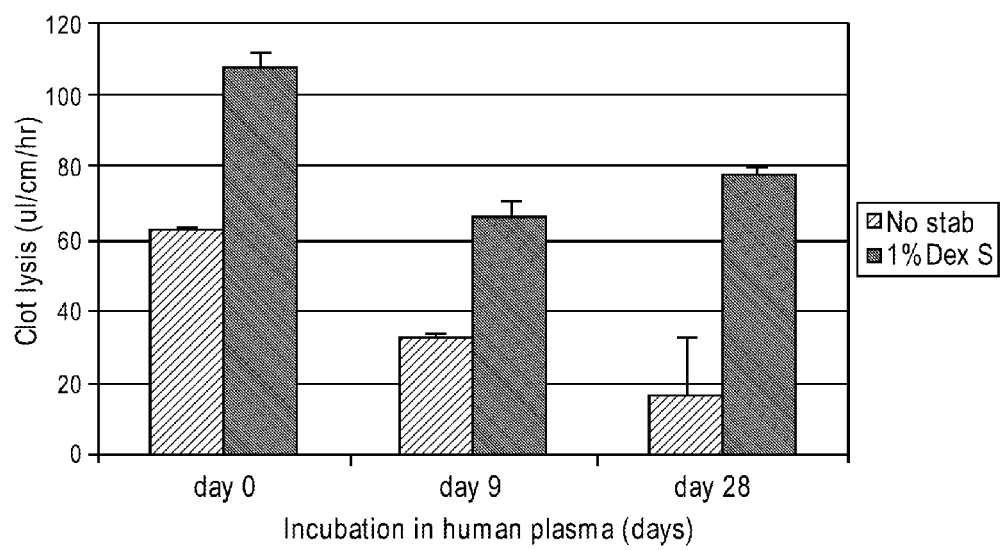
FIG. 6 is a graph showing fibrinolytic activity of uPA immobilized on ehlorhexidine coated polyurethane catheter segments and stabilized with low molecular weight dextran sulfate, human serum albumin, and the amino acid arginine following incubation times ranging from 0 to 28 days.

Evaluating the Duration of Enzymatic Activity from the Low Molecular Weight Dextran Sulfate Stabilized Catheter Segments Containing an Antimicrobial Agent To evaluate the durability of the 1% LMW-DexS (8 kDa) treated catheters segments containing the antimicrobial agent, CHA, and immobilized enzyme, uPA, the catheter segments were incubated at 37° C. in citrated human plasma for different time periods. The citrated human plasma was replaced with fresh sample after every 7 days. As shown in FIG. 6, the 1% LMW-DexS (8 kDa) treated catheters segments retained approximately 80% of the enzymatic activity after 28 days. That is, the 1% LMW-DexS (8 kDa) stabilized and immobilized uPA enzyme remained active for 28 days in human plasma substantially without any loss in the activity compared to the control. These results were particularly unexpected in light of the approximately 90+% loss in activity shown in FIGS. 1 and 6 for un-stabilized uPA.

Experiment 7

Evaluating Antimicrobial Activity for Low Molecular Weight Dextran Sulfate Stabilized Catheter Segments Containing Antimicrobial Agents In addition to fibrinolytic activity, antimicrobial activity of the 1% LMW-DexS (8 kDa) treated catheters was evaluated. In this test, adherence of gram positive bacteria *Staphylococcus aureus* ATCC 33591, on the catheter segments having immobilized enzyme uPA stabilized with 1% LMW-DexS (8 kDa), along with the antimicrobial agents such as gentian violet (0.6%) and chlorhexidine dodecanoate was compared to similarly treated catheter segments but without the LMW-DexS (8 kDa) stabilized enzyme. A five log reduction in adherence of the bacteria was observed on both catheter types, i.e. either with or without LMW-DexS (8 kDa). Thus, the antimicrobial activity of gentian violet and chlorhexidine dodecanoate against the tested organisms was not compromised due to the attachment of LMW-DexS (8 kDa) stabilized urokinase.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A medical device, comprising:
   a base material; and
   an immobilized enzyme covalently bound to the base material in the presence of dextran sulfate,
   wherein the medical device is configured to be implanted in the vascular system of a patient, and
   wherein the dextran sulfate has a molecular weight of about 8 kilodaltons (kDa) to stabilize the immobilized enzyme when in contact with blood of the patient.

2. The medical device according to claim 1, wherein the immobilized enzyme includes at least one of:
   a blood clot digestive enzyme including one or more of:
      a urokinase-type plasminogen activator (uPA);
      a tissue plasminogen activator (tPA); and
      a streptokinase; and
   an extracellular matrix digestive enzyme including one or more of:
      a protease;
      an aminopeptidase;
      a collagenase;
      a matrix metalloproteinase;
      a metalloendopeptidase;
      a serine endopeptidase;
      a hydrolase;
      a glucuronidase;
      a hyaluronoglucosaminidase;
      a heparanase;
      a cathepsin;
      a hyaluronidase; and
      a matriptase.

3. The medical device according to claim 1, further comprising:
   a combination of two or more antimicrobial agents impregnating the base material.

4. The medical device according to claim 3, wherein the combination of two or more antimicrobial agents includes:
   a pharmaceutically acceptable salt of a bis-biguanide including at least one of:
      a chlorhexidine base; and
      an alexidine; and
   a guanide including polyhexamethylene biguanide (PHMB).

5. The medical device according to claim 1, further comprising:
an antimicrobial agent impregnating the base material.

6. The medical device according to claim 5, wherein the antimicrobial agent includes:
a chlorhexidine base;
a pharmaceutically acceptable salt of a chlorhexidine base;
chlorhexidine diacetate;
alexidine; or polyhexamethylene biguanide (PHMB).

7. The medical device according to claim 1, wherein at least a part of the medical device has a tubular structure including the base material.

8. The medical device according to claim 1, wherein the base material is a polymer.

9. The medical device according to claim 8, wherein the polymer is a polyurethane.

10. A medical device, comprising:
a polyurethane base material configured to be implanted in the vascular system of a patient;
an amount of a blood clot digestive enzyme sufficient to reduce the formation of device related blood clots and an amount of an extracellular matrix digestive enzyme sufficient to reduce neo-initimal hyperplasia, the enzymes being immobilized on the medical device by covalently binding the enzymes to the polyurethane base material;
a low molecular weight dextran sulfate configured to stabilize the enzymes when in contact with blood of the patient, the low molecular weight dextran sulfate having a molecular weight of about 8 kilodaltons; and
an antimicrobial agent disposed in the polyurethane base material in an amount sufficient to reduce microbial growth.

11. A medical device comprising:
a polyurethane base material configured to be implanted in the vascular system of a patient;
an amount of an enzyme sufficient to reduce the formation of blood clots in a patient or sufficient to reduce neo-initimal hyperplasia, the enzyme being covalently immobilized in the base material;
a low molecular weight dextran sulfate configured to stabilize the enzyme when in contact with blood of the patient, the low molecular weight dextran sulfate having a molecular weight of about 8 kilodaltons; and
a chlorhexidine base or a pharmaceutically acceptable salt thereof disposed in the polyurethane base material in an amount sufficient to reduce microbial growth.

12. A medical device, comprising:
a base material;
an immobilized enzyme covalently bound to the base material in the presence of dextran sulfate; and
a cationic selective antimicrobial impregnating the base material,
wherein the medical device is configured to be implanted in the vascular system of a patient, and
wherein the dextran sulfate has a molecular weight of about 8 kilodaltons (kDa) to stabilize the immobilized enzyme when in contact with blood of the patient.

13. The medical device according to claim 12, wherein the immobilized enzyme includes at least one of:
a blood clot digestive enzyme including one or more of:
a urokinase-type plasminogen activator (uPA);
a tissue plasminogen activator (tPA); and
a streptokinase; and
an extracellular matrix digestive enzyme including one or more of:
a protease;
an aminopeptidase;
a collagenase;
a matrix metalloproteinase;
a metalloendopeptidase;
a serine endopeptidase;
a hydrolase;
a glucuronidase;
a hyaluronoglucosaminidase;
a heparanase;
a cathepsin;
a hyaluronidase; and
a matriptase.

14. The medical device according to claim 12, wherein at least a part of the medical device has a tubular structure including the base material.

15. The medical device according to claim 12, wherein the base material is a polymer.

16. The medical device according to claim 15, wherein the polymer is a polyurethane.

17. The medical device according to claim 12, wherein the cationic selective antimicrobial is a ceragenin.

18. The medical device according to claim 12, wherein the cationic selective antimicrobial is in an amount sufficient to reduce microbial growth.

* * * * *